United States Patent [19]

Golwyn

[11] Patent Number: 5,147,872
[45] Date of Patent: Sep. 15, 1992

[54] TREATMENT OF IMMUNOLOGICALLY BASED DISORDERS, SPECIFICALLY PSORIASIS

[76] Inventor: Daniel H. Golwyn, P.O. Box 151408, Altamonte Springs, Fla. 32715-1408

[21] Appl. No.: 540,538

[22] Filed: Jun. 19, 1990

Related U.S. Application Data

[63] Continuation-in-part of Ser. No. 59,899, Jun. 9, 1987, Pat. No. 5,017,575.

[51] Int. Cl.$^5$ .................... A01N 43/62; A61K 31/55
[52] U.S. Cl. .................................. 514/219; 514/220
[58] Field of Search .............................. 514/220, 219

*Primary Examiner*—Nathan M. Nutter
*Attorney, Agent, or Firm*—Charles A. McClure

[57] ABSTRACT

Methods and means for treating psoriasis, as well as Crohn's disease and other HLA-related disorders, to abate their symptoms, with a pharmaceutical diazepine having a component triazolo ring. HLA-related disorders amenable to such treatment include (i) persistent eruptive, granular, or ulcerative conditions of the skin, mouth, or gastrointestinal tract; and (ii) dibilitating inflammatory conditions of the circulatory, muscular, and nervous systems. This treatment alleviates abnormality or unbalance of patients' immune systems, such as an overabundance of natural killer cells and/or an abnormality of helper T-cell/suppressor T-cell ratio, and alleviates the self-cannibilism of the Koebner phenomenon, when present. Triazolobenzodiazepines, such as alprazolam or triazolam, and triazolothienodiazepines, such as etizolam, are examples of preferred treating compositions.

9 Claims, 2 Drawing Sheets

FIG. 1
FIG. 2

TREATMENT OF IMMUNOLOGICALLY BASED DISORDERS, SPECIFICALLY PSORIASIS

This is a continuation-in-part of my copending application, Ser. No. 059,889, filed Jun. 9, 1987, now U.S. Pat. No. 5,017,575.

TECHNICAL FIELD

This invention relates to treatment of psoriasis, as an example of human disorders such as have an apparently immunological basis defined as detailed below; it concerns especially alleviating the symptoms of patients having autoimmune system disorders, by treating them with certain drugs.

BACKGROUND

Many people suffer chronically from very persistent eruptive, granular, or ulcerative conditions, such as of the skin, mouth, or gastrointestinal tract. Other (sometimes the same) persons suffer from debilitating inflammatory conditions, such as disorders of the circulatory, muscular, and nervous systems. Examples of the first general category include alopecia, psoriasis, mouth ulcers, Crohn's disease, or ulcerative colitis, and examples of the second general category include arthritis, rheumatism, discoid and systemic lupus erythematosa, and muscular dystrophy. Persons so afflicted range from uncomfortable and often somewhat disfigured, to very miserable, and on to life-threatened—unless or until such condition abates.

Although sometimes such disorders may be alleviated more or less in one way or another, hitherto no readily effective treatment has been known for them individually, much less generally. Perhaps because of the lack of a recognized potentially successful treatment, many such disorders are deemed to be idiopathic. Indeed, insult may be added to injury, as unsympathetic persons characterize such patients as "mental" cases responsible—if only involuntarily—for their own condition or symptoms.

A putatively more enlightened view is that such disorders are human leucocyte antigen (HLA) related, stemming from some unbalance or malfunction of the autoimmune system. Many are so classified by one or another medical authority. Several dozen, including all or most of those listed above, are so characterized in CECIL'S TEXTBOOK OF MEDICINE, edition of 1985, for example. Many of them exhibit the Koebner phenomenon, wherein bits of otherwise normal tissue released into the bloodstream of their host, as by some trauma, are erroneously treated as antigens by the host's autoimmune system, with resultant damage to tissues of such host. However, the present example is psoriasis, evident as an eruptive manifestation of the skin.

A summary, relatively non-technical introduction to the human immune system, describing the respective functions of the various white blood cells or lymphocytes, with illustrative graphics, is found in the NATIONAL GEOGRAPHIC, Vol. 169, No. 6, Jun. 1986.

My invention is directed to relieving at least the symptoms of such disorders, which are noted for their intractability under conventional treatment, thereby to enhance the quality of life of those persons so afflicted, while they are awaiting recovery from—or more overt correction of—their underlying autoimmune malfunctioning.

In addition to treatment of Crohn's disease, an affliction of the digestive tract (to which my aformentioned patent application was particularly directed), my invention is exemplified here by such treatment of psoriasis, a persistent reddening and eruptive condition of the skin. Crohn's disease and psoriasis often exist apart from one another, but sometimes both are present in the same person.

SUMMARY OF THE INVENTION

A primary object of the present invention is to relieve the symptoms psoriasis as an prominent example of of art-recognized HLA-related disorders of the human (or comparable mammalian) autoimmune system.

Another object of this invention is to counteract various manifestations of the Koebner phenomenon in human patients.

Yet another object of the invention is to reduce the concentration of natural killer cells in patients subject to disorders characterized by an abnormally high concentration of such cells.

A further object of the invention in treating HLA-related disorders is to restore the ratio of helper T-cells to suppressor T-cells in the direction of normality in patients whose immune systems are characterized by an abnormal ratio thereof.

Yet another object of the present invention is to increase the concentration ratio of helper T cells to killer T cells by changing either or both of such concentrations in the appropriate direction.

In general, my invention resides in administering to patients having HLA-related disorders characterized by deleterious abnormal autoimmune reactions evident as persistent eruptive, granular, or ulcerative conditions, or as debilitating inflammatory conditions, a drug effective to reduce the incidence or the severity of their symptoms to tolerable levels, preferably to eliminate such symptoms.

More particularly, the invention comprises alleviating psoriasis symptoms, attributable at least in part to a patient's own immunological abnormality or unbalance—often evident from abnormal concentrations of various white blood cells—as by administering thereto a composition having a triazolo group, such as a triazolobenzodiazepine or a triazolothienodiazepine. Such a composition may already have another accepted pharmacological utility.

Other objects of this invention, together with methods and means for accomplishing the various objects, will be apparent from the following description of preferred embodiments and variants, which are presented here by way of example rather than limitation.

BRIEF DESCRIPTION OF THE DRAWINGS

FIG. 1 is an abdominal radiographic view of a Crohn's disease patient before treatment according to the present invention; and FIG. 2 is a similar view of the same human patient, taken after treatment according to this invention.

DESCRIPTION OF THE INVENTION

Figure 3:
FIG. 3 is a photographic view of another human patient showing psoriasis on and about an elbow and forearm.

The present invention undertakes to modify autoimmune activity of humans (and comparable mammals) so as to remedy systemic defects or functional errors whose causes or origins are not yet well understood. It is a fundamentally therapeutic method, whose scope is dependent upon factors remaining to be ascertaine. In the present developmental stage of this method, theoretical statements made herein must be incomplete and may be erroneous in some respects. However, as the therapeutic effects of the invention are obtainable in practice, rather than dependent upon any specific theory, the inventive method should not be prejudiced by whatever academic or theoretical shortcomings this specification may exhibit, whether in mention of apparent immunological linkages of any given disorder or any academic or theoretical explanation or suggestion.

Benzodiazepines constitute a well recognized class of cyclic organic chemicals for which methods of preparation and therapeutic utility also are well known. See, for example, such U.S. patents as U.S. Pat. No. 2,893,992 for chlordiazepoxide; U.S. Pat. No. 3,516,988 for clorazepate; U.S. Pat. Nos. 3,102,116, 3,109,843, and 3,136,815 for diazepam; U.S. Pat. No. 3,296,249 for lorazepam; U.S. Pat. Nos. 3,109,843 and 3,340,253 for oxazepam, and U.S. Pat. Nos. 3,192,199 and 3,192,200 for prazepam. Under various brand names, these are accepted as tranquilizers or like agents and are 1,4-diazepines with 7-chloro, 5-phenyl substituents with or without other substituents of whatever types in some of the lower numbered positions. Perhaps the best known of the benzodiazepines is diazepam, well known under the brand name "Valium" (Hoffman La Roche). Most, if not all, of these compositions are rather mildly addictive.

Benzodiazepines are well accepted as depressants of the central nervous system, and are used customarily in treating patients with symptoms ranging from anxiety to panic/ Hitherto, such compositions have not been recognized as useful in treating immunological unbalance, such as may give rise to disorders in the aforementioned categories, or in regard to less specific immunological depression or suppression, such as are customarily treated with one or another analgesic, emollient, hormone, or steroid, for example.

Thienodiazepines constitute another recognized class of cyclic organic chemicals for which methods of preparation and therapeutic utility also are well known. They differ from the benzodiazepines by havin—in place of the 6-membered benzo ring—a five-membered thieno ring (with the S in the last position).

Another set of 1,4-benzodiazepines differs by having a five-membered triazolo ring formed along the former 1,2 side, including the pre-existing nitrogen See U.S. Pat. Nos. 3,701,782 and 3,987,052 for the preparation of such compositions The members of this set that have both 8-chloro and 1-methyl groups and are, respectively, 6-phenyl- and 6-chlorophenyl-substituted are known as alprazolam and triazolam. They are similarly used under the respective brand names of "Xanax" and "Halcion" (both Upjohn) Use of them and of related triazolo compositions, e.g., to induce sleep, is disclosed in U.S. Pat. Nos. 3,980,789 and 3,980,790. Estazolam from U.S. Pat. No. 3,701,782 lacks the usual chloro substituent(s).

Triazolothienodiazepines are disclosed, for example, in U.S. Pat. Nos. 3,701,782, 3,904,641 and 4,017,620. These compositions also are used to treat anxiety and the like. An example is etizolam, which is 1-methyl-6-o-chlorophenyl-8-ethyl-4H-s-triazolo- [4,3-a]-thieno-[3,2-f][1,4]diazepine (not to be confused with estazolam, a triazolobenzodiazepine similar to alprazolam but without a 1-methyl group). A report by Tahara and co-authors characterizing such compositions as also being antagonists to blood platelet activating factor (PAF) is found in Communications to the Editor, CHEM. PHARM. BULL. vol. 35, pages 2119–2121 (1987).

The just mentioned triazolobenzodiazepines and triazolothienodiazepines are useful in or according to the present invention, as described further below. Moreover, so far as is known, none of these diazepines lacking the triazolo ring is effective against the disorders to which this invention is directed.

Indeed, experimental patients successfully treated according to the present invention who temporarily discontinued such treatment and substituted readily available triazolo-free tranquilizers of their choice suffered recurrence of the symptoms they had just been rid of, whereupon resumption of treatment with a composition of this invention at a low or maintenance-level dosage again rid them of such symptoms and kept them symptom-free.

FIGS. 1 and 2 are abdominal radiographic views of a person with a history (at least ten years) of recurrent psoriasis and chronic ileitis and were taken, respectively, before and after treatment according to the present invention. Visible in both views are a plurality of staples 11, which were introduced upon previous resection of the small intestine. As is common in such disorder, removal of of an affected portion of the intestine was followed by a like disorder of at least part of the remainder. FIG. 1 shows some twenty centimeters of diseased terminal ileum 15 at the left center. The affected portion is narrowed, with an irregular outline characteristic of extreme ulceration. First, this patient was weaned from all other medication. Then she was given alprazolam daily in increasing dosage, which peaked at 7 milligrams. Within several weeks, after substantial reduction in symptoms, such dosage was reduced by a half milligram every several days to less than a single mg daily to maintain her symptom-free. Drowsiness was the only significant side effect. FIG. 2 was taken four months later, when her psoriasis and intestinal distress had disappeared. This view shows a normally wide smooth appearance of the formerly diseased part, and the fact of complete healing was confirmed by internal examination.

Also illustrated here is psoriasis in two patients treated for it according to this invention. Although black-and-white views show the reddening that is characteristic of psoriasis only indirectly, as a darkening, they display its characteristic eruptive appearance.

Figure 4:
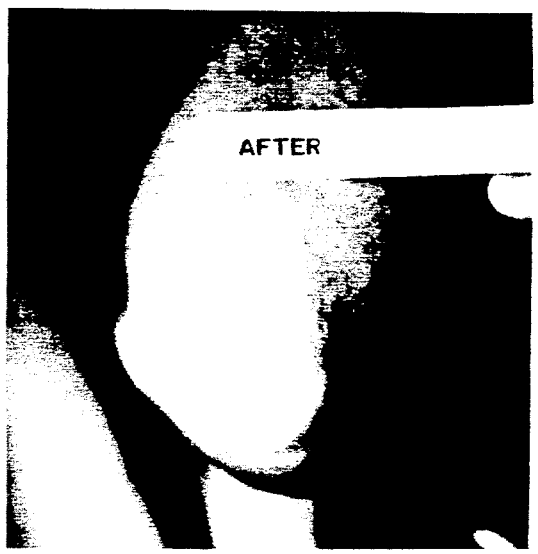
FIG. 4 is a similar view of the same patient's same elbow and arm, after treatment according to this invention.

FIGS. 3 and 4 are views of the same patient's psoriasis "before" and "after" being simultaneously alleviated by the same treatment This is an example of plural species of the eruptive, granular, ulcerative category or sub-genus in a single person. FIG. 3 shows the eruptive appearance of the elbow and forearm of a first additional psoriasis patient as it appeared initially, whereas FIG. 4 is a like view of the same region taken four and one-half months after beginning treatment according to this invention, evidencing virtual disappearance of the red eruptions. The maximum daily dosage was about 10 milligrams, and ultimately less than a mg.

Figure 5:
FIG. 5 is a photographic view of yet another human patient with psoriasis of the palm of the hand.
Figure 6:
FIG. 6 is a similar view of the same patient's same hand, after treatment according to this invention.

FIG. 5 shows the palm of an additional psoriasis patient as it appeared initially, reddened (dark tone) and roughened by eruptions in the center of the palm and elsewhere, whereas FIG. 6 is a like view of the same palm taken after of this treatment, and the palm is seen to be light and smooth. This patient had a 30-year history of recurrent psoriasis; he was rid of it in less than 3 months, subject to a continuing fractional mg. maintenance dosage daily.

Effective compositions for use according to this invention are triazolo-substituted (benzo or thieno) diazepines. Specific compositions of preference for use herein are alprazolam, triazolam, and etizolam, including their pharmacologically acceptable acid addition salts and N-oxides in combination with a pharmaceutical carrier. Preferred compositions include 8-chloro-1-methyl-6-phenyl-4H-s-triazolo[4,3-a][1,4]-benzodiazepine; 8-chloro-6-(o-chlorophenyl)-1-methyl-4H-s-triazolo[4,3-a][1,4]-benzodiazepine; and 1-methyl-6-(o-chlorophenyl)-8-ethyl-4H-s-triazolo-[4,3-c]-thieno-[3,2-f][1,4]diazepine. These are known pharmaceuticals, whose preparation and conventional uses are disclosed in the aforementioned U.S. patents.

The customary dosage of alprazolam according to this invention is from about a half dozen to one and one-half dozen milligrams per day, usually orally in a single capsule or tablet. An initial dosage of up to a mg can be readily stepped up to such customary dosage—or even to a peak that may exceed the customary dosage by up to about 50%—and after an effective period of time be stepped down to maintenance dosage. Gradual reduction, such as a half milligram every several days, is desirable to minimize withdrawal symptoms in event of addiction. The need for a continuing minimal dosage to prevent recurrence of symptoms indicates that whatever causes these disorders is in some way interfered with by treatment according to this invention, but the potential for producing such symptoms is not eliminated. In other words, this treatment is an alleviant, not a cure, although some patients have substantial periods of remission. Minimal maintenance dosage varies with the disorder and the patient, often being a minor fraction of a milligram, usually no more than one but sometimes as high as several mg. per day.

Dosages of other triazolobenzodiazepines may be less than for alprazolam, whether because of enhanced efficacy or greater side effects, as in the instance of triazolam. Triazolothienodiazepines, such as etizolam, having been shown superior by more than an order of magnitude in PAF inhibition, should be administered accordingly.

What appears to be involved in treatment according to this invention is suggested by lymphocyte profiles obtained for patients so afflicted, which usually show an abnormally high percentage of natural killer cells, viz., more than an acceptable maximum in the mid-teens—as % of all lymphocytes. This treatment has been observed to lower such killer cell concentration in such patients, as by as much as one-half of an abnormally high percentage, restoring it to the normal range. Concentrations of helper and/or suppressor T cells usually are abnormal, as is the helper-to-suppressor ratio. The same treatment also been observed to restore such concentrations and such ratio to or toward normal levels.

Until a more effective method is discovered, such as actually preventing occurrence of such an immunological unbalance—which so often gives rise to injury or destruction of the host's own normal tissues—this treatment will enable such self-damage potential to be offset, perhaps indefinitely into the future. The consequences for the afflicted patient are obviously very beneficial. Alternative available and suitable pharmaceutical compositions are noted above.

Effectively treated with such suitable pharmacological compositions according to this invention have been such disorders of the skin, mouth, and gastro-intestinal tract as alopecia, psoriasis, recurrent aphthous stomatitis (mouth ulcers), ulcerative colitis, and Crohn's disease; and likewise such debilitating disorders such as multiple sclerosis, myasthenia gravis, discoid and systemic lupus erythematosis, and polymalgia rheumatica. Reduction in killer T-cell concentration appears to leave only enough such cells to perform their normal functions, as upon high-priority exogenous matter, with the host's own tissues formerly attacked being ignored unless and until the killer T-cell concentration should rise again, as upon discontinuation of the treatment. Other types of immunological abnormality or unbalance for the application of this invention include (a) allergies, wherein immunoglobulins react to pollens and other relatively innocuous allergens but annoy the host by releasing histamines, etc.; and (b) depressed or suppressed immune systems, such as have been subjected to chemotherapy and (c) those undergoing viral attack of such nature or intensity as to interfere with or overwhelm the functioning of the immune system, such as in certain herpes and influenza strains.

Advantages of this invention are obvious, in view of the extremely injurious or deadly nature of the disorders amenable to treatment by the compositions and the methods of this invention. Specific therapeutic benefits have been mentioned hereinabove. Modifications may be made, as by adding, combining, or subtracting compositions or substituents of compositions, or by otherwise varying the treatment method disclosed herein, while retaining at least some of the benefits of the present invention, which itself is defined in the following claims.

I claim:

1. A method of treating patients having a human leukocyte antigen (HLA) related disorder, with symptoms of psoriasis,
   comprising orally administering to such a patient an amount of the triazolothienodiazepine alprazolam effective to alleviate such psoriasis symptoms.

2. A method of treating patients having a human leukocyte antigen (HLA) related disorder, with symptoms oif psoriasis, comprising orally administering to such a patient an amount of the triazolothienodiazepine etizolam effective to alleviate such psoriasis symptoms.

3. Method of treating for psoriasis patients whose lymphocyte profiles show an abnormally high initial concentration of natural killer cells,
   comprising orally administering to such a patient an amount of a composition selected from the group consisting of alprazolam, etizolam, and triazolam effective to reduce such abnormally high killer concentration toward a more normal value thereof.

4. Method according to claim 3, including so administering 8-chloro-1-methyl-6-phenyl-4-H-s-triazolo-[1,4]-benzodiazepine.

5. Method according to claim 3, including so administering 8-chloro-1-methyl-6-(o-chlorophenyl)-4H-s-triazolo[1,4]-benzodiazepine.

6. Method according to claim 3, including so administering 1-methyl-6-o-chlorophenyl-8-ethyl-4-H-s-triazolo-4,3-a]-thieno[3,2-f][1,4]-diazepine.

7. Method of treating for psoriasis patients whose lymphocyte profiles show an abnormally high initial concentration of natural killer cells.
comprising orally administering to such a patient an amount of a composition selected from the group consisting of alprazolam, etizolam, and triazolam effective to reduce such abnormally high killer concentration toward a more normal value thereof,
wherein Chrohn's disease is present in the same patient.

8. Method of treating patients for the symptoms of psoriasis, comprising administering to such a patient an amount of alprazolam, etizolam, or triazolam effective to abate the psoriasis symptoms, wherein daily dosage of such composition rises to a maximum between about a half dozen to one and one-half dozen milligrams, then continues at such level until marked reduction in symptoms, and finally is reduced to a symptom-free maintenance level of at least a minor fraction of a milligram and at most about one milligram.

9. Method according to claim 8, including continuing such maintenance dosage as necessary to preclude or abate recurrence of the psoriasis.

* * * * *